United States Patent
Alawneh et al.

(10) Patent No.: US 12,030,911 B2
(45) Date of Patent: Jul. 9, 2024

(54) SYNTHESIS AND BIOLOGICAL ACTIVITY OF PHOSPHORAMIDIMIDATE AND PHOSPHORAMIDATE DNA

(71) Applicant: The Regents of the University of Colorado, a body corporate, Denver, CO (US)

(72) Inventors: Ayman Alawneh, Boulder, CO (US); Marvin Caruthers, Boulder, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 729 days.

(21) Appl. No.: 17/251,608

(22) PCT Filed: Jun. 14, 2019

(86) PCT No.: PCT/US2019/037346
§ 371 (c)(1),
(2) Date: Dec. 11, 2020

(87) PCT Pub. No.: WO2019/241729
PCT Pub. Date: Dec. 19, 2019

(65) Prior Publication Data
US 2021/0277047 A1    Sep. 9, 2021

Related U.S. Application Data

(60) Provisional application No. 62/685,852, filed on Jun. 15, 2018.

(51) Int. Cl.
*C07H 21/04* (2006.01)
*C07H 1/00* (2006.01)
*C07H 19/073* (2006.01)

(52) U.S. Cl.
CPC .............. *C07H 21/04* (2013.01); *C07H 1/00* (2013.01); *C07H 19/073* (2013.01)

(58) Field of Classification Search
CPC .............................. C07H 21/04; C07H 19/073
See application file for complete search history.

(56) References Cited

U.S. PATENT DOCUMENTS

2009/0318676 A1   12/2009   Manoharan et al.

FOREIGN PATENT DOCUMENTS

WO   2017037141 A1   3/2017

OTHER PUBLICATIONS

Caruthers, M. H. et al., Methods in Enzymology, "Chemical Synthesis of Deoxyoligonucleotides by the Phosphoramidite Method", 1985, vol. 230, pp. 281-313 (Year: 1985).*

(Continued)

*Primary Examiner* — Bahar Craigo
(74) *Attorney, Agent, or Firm* — Berg Hill Greenleaf Ruscitti LLP

(57) ABSTRACT

Oligonucleotides comprising phosphoramidimidate internucleotide linkages, and methods of efficiently synthesizing these oligonucleotides with high yield are provided. These oligonucleotides form duplexes with complementary DNA or RNA that are more stable than natural DNA or DNA/RNA complexes, are active with RNAse H1, and may be transfected into cells using standard lipid reagents. These analogues are therefore useful for numerous therapeutic antisense applications.

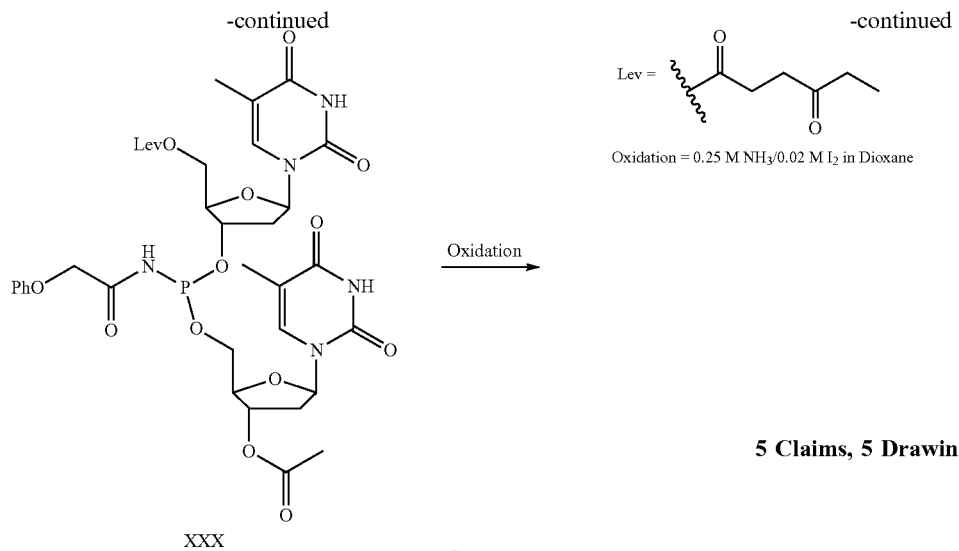

5 Claims, 5 Drawing Sheets

(56) References Cited

OTHER PUBLICATIONS

Bjergarde, K. et al., Tetrahedron Letters, "Synthesis of Dinucleoside Phosphoramidimidates", 1994, vol. 35, No. 18, pp. 2941-2944 (Year: 1994).*

Alawneh, AG. "Synthesis and Biochemical Evaluation of Aminoboranephosphonate Phosphoramidimidate and Phosphoramidate DNA"; pp. 1-208 [online], [retrieved on Aug. 29, 2019). Retrieved from the Internet <URL: https ://pdfs. semanticscholar. org/3 7 0a/50a6 73e08fbc5063034b 15b242f 56144fd43. pdf>; p. 11, second paragraph; p. 60, figure 4.2; p. 60, figure 4.3; p. 85, figure 5.3; p. 85, first paragraph; p. 86, figure 5.4; bage 112, first paragraph, 70 pages.

International Search Report dated Oct. 16, 2019 in International Application No. PCT/US19/37346, 2 pages.

* cited by examiner ized with a trimethoxytrityl
SYNTHESIS AND BIOLOGICAL ACTIVITY OF PHOSPHORAMIDIMIDATE AND PHOSPHORAMIDATE DNA

CROSS REFERENCE TO RELATED APPLICATION

This application is a national stage application under 35 U.S.C. 371 of PCT Application No. PCT/US2019/037346 having an international filing date of Jun. 14, 2019, which designated the United States, which PCT application claimed the benefit of U.S. Application Ser. No. 62/685,852, filed Jun. 15, 2018, both of which are incorporated by reference in their entirety.

TECHNICAL FIELD

This disclosure relates to methods of synthesizing oligonucleotides comprising phosphoramidimidate internucleotide linkages, and derivatives thereof.

BACKGROUND

Morpholino oligonucleotides show promise for use as antisense oligonucleotide therapeutics due to their high affinity for DNA and RNA, resistance to various nucleases, stability in vivo, and low toxicity.

Oligonucleotides comprising phosphoramidimidate internucleotide linkages have nonionic inter-nucleotide linkages may be used to inhibit gene expression by preventing translation while interfering with RNA-splicing. Therapeutic development of these backbone-modified oligonucleotides is underway, for example in clinical trials for the treatment of Duchenne Muscular Dystrophy (DMD), and preventing infection of the hemorrhagic Filovirus Marburg (US Patent Publications 2016/0040162 and 2015/0038462).

Unfortunately, these promising applications are limited by the lack of an efficient synthesis methodologies. In contrast to standard methods for chemically preparing DNA and RNA on an automated synthesizer, PMOs are currently synthesized in a 5' to 3' direction on a silica gel (Fischer and Caruthers, Tetrahedron Letters, 1995, 36(38):6807-10).

The synthesis methods of this disclosure achieve significant advantages over the prior art methods.

SUMMARY

This disclosure provides new methods for synthesizing oligonucleotides comprising phosphoramidimidate internucleotide linkages (PIOs) and PIO-DNA chimeras. These methods are very robust as oligomers containing phosphosphorodiamidate internucleotide linkages can be prepared using phosphoramidite chemistry, in high yield on automated DNA synthesizers. The process begins by incorporating phosphoramidimidate internucleotide linkages into DNA, oxidation with iodine, and deprotection of the ribose base in order to form a diverse set of PIOs and/or PIO-DNA chimeras. The method is general and leads to the synthesis of a large number of antisense oligonucleotides comprising phosphoramidimidate internucleotide linkages in high yields.

Advantageously, the PIO and PIO-DNA chimeras may be synthesized on a DNA synthesizer in a 3' to 5' direction, which is not the case with previously developed chemistries.

Relative to their potential use in various biological and biochemical applications, these PIO and PIO-DNA chimeras exhibit advantages over several other analogues. For example, PIO-DNA chimeras form a more stable duplex with complementary DNA or RNA than either unmodified DNA/RNA or the standard N,N-dimethylamino PMO analogues. Additionally, these PIO-DNA chimeras are active with RNAse H1. This is encouraging relative to the standard N,N-dimethylamino PMO analogs in which the completely substituted PMO is inactive with RNase H1. Due to the increased stabilization of these PIO-DNA chimeras with complementary RNA (relative to the unmodified duplexes), these analogues decrease off-target effects because shorter, single-stranded antisense oligonucleotides can be used. Moreover, these PIO-DNA chimeras can easily be transfected into cells using common, well known transfecting reagents, which eliminates problems associated with delivery of PIOs by such procedures as microinjection, hybridization of PMOs with DNA and delivery with ethoxylated polyethylenimine, or conjugation with either peptides, or dendritic molecular transporters.

Thus, this disclosure provides PIO synthesis methodologies that provide efficient and cost-efficient methods of synthesizing PMO derivatives with the formation of few side products.

This Summary is neither intended nor should it be construed as being representative of the full extent and scope of the present invention. Moreover, references made herein to "the present disclosure," or aspects thereof, should be understood to mean certain embodiments of the present disclosure and should not necessarily be construed as limiting all embodiments to a particular description. The present disclosure is set forth in various levels of detail in this Summary as well as in the attached drawings and the Description of Embodiments and no limitation as to the scope of the present disclosure is intended by either the inclusion or non-inclusion of elements, components, etc. in this Summary. Additional aspects of the present disclosure will become more readily apparent from the Description of Embodiments, particularly when taken together with the drawings.

DESCRIPTION OF EMBODIMENTS

Figure 1:
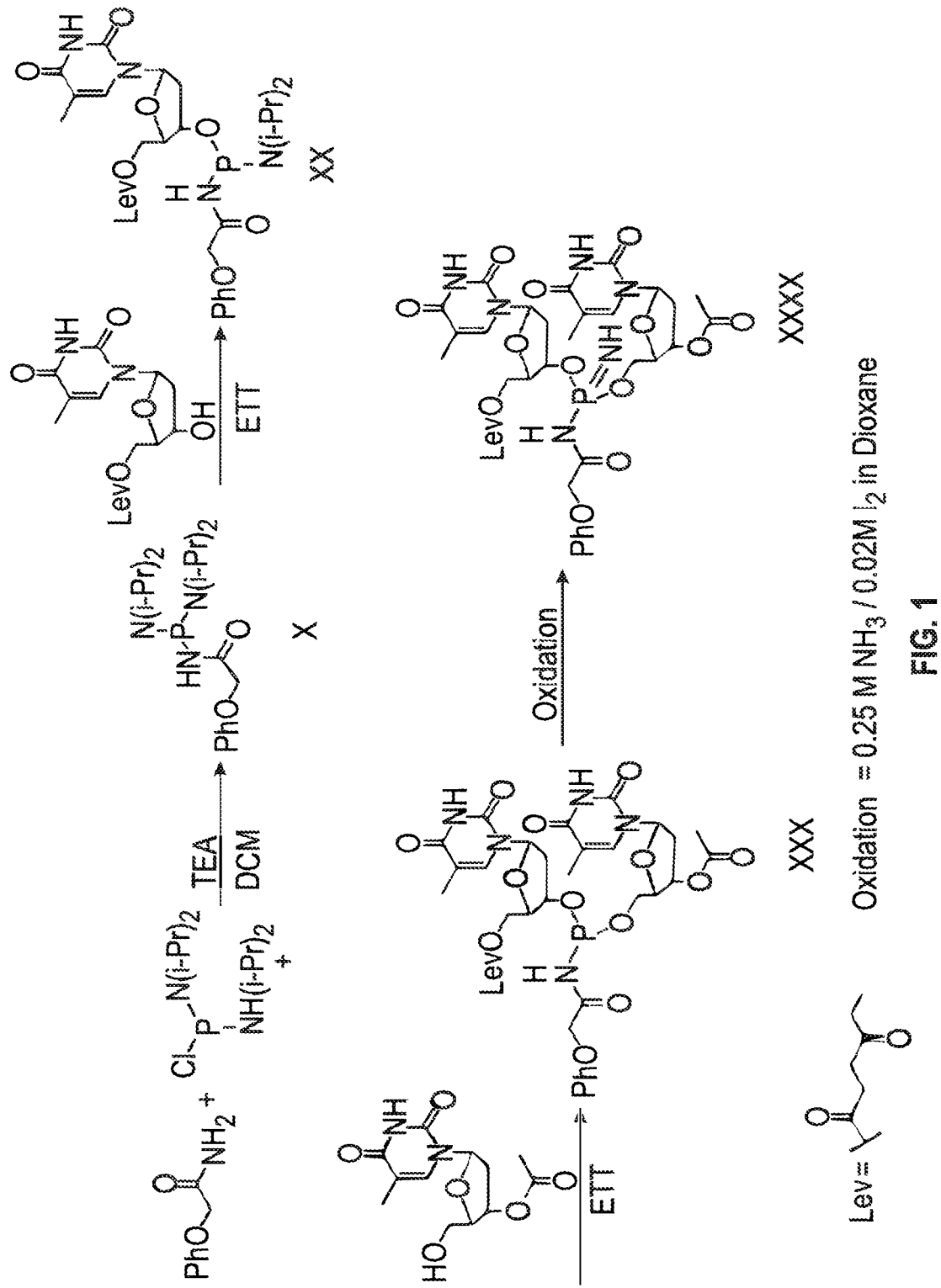
FIG. 1 is a synthesis scheme for production of the chemical synthon compounds X-XXX used to prepare dithymidine-containing phosphoramidimidate internucleotide linkage N-protected with a phenoxyacetyl group.

The terms below have the following meanings, unless indicated otherwise:

The term "oligonucleotide analog" refers to oligonucleotide having a modified backbone structure, e.g., a backbone other than the standard phosphodiester linkage found in natural oligo- and polynucleotides, and optionally, modified sugar moieties, e.g., morpholino moieties rather than ribose or deoxyribose moieties. The analog supports bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

A "nucleic acid base" is not particularly limited as long as it can be used for the synthesis of nucleic acid and includes, for example, a pyrimidine base such as cytosyl group, uracil group, thyminyl group and the like, and a purine base such as adenyl group, guanyl group and the like. The "optionally protected nucleic acid base" means, for example, that an amino group may be protected in an adenyl group, a guanyl group or a cytosyl group, which is a nucleic acid base having an amino group, and a nucleic acid base wherein the amino group therein is protected by a protecting group sustainable under the deprotection conditions of the morpholine ring nitrogen atom of the morpholino nucleotide is preferable.

The "amino-protecting group" is not particularly limited, and examples thereof include the protecting groups described in Greene's PROTECTIVE GROUPS IN ORGANIC SYNTHESIS, 4th edition, Wiley-Interscience, 2006 and the like. Specific examples of the "amino-protecting group" include a pivaloyl group, a pivaloyloxymethyl group, a trifluoroacetyl group, a phenoxyacetyl group, a 4-isopropylphenoxyacetyl group, a 4-tert-butylphenoxyacetyl group, an acetyl group, a benzoyl group, an isobutyryl group, a dimethylformamidinyl group, a 9-fluorenylmethyloxycarbonyl group and the like. Among them, a phenoxyacetyl group, a 4-isopropylphenoxyacetyl group, an acetyl group, a benzoyl group, an isobutyryl group and a dimethylformamidinyl group are preferable. In addition, the carbonyl group of the nucleic acid base is optionally protected, and can be protected, for example, by reacting phenol, 2,5-dichlorophenol, 3-chlorophenol, 3,5-dichlorophenol, 2-formylphenol, 2-naphthol, 4-methoxyphenol, 4-chlorophenol, 2-nitrophenol, 4-nitrophenol, 4-acetylaminophenol, pentafluorophenol, 4-pivaloyloxybenzyl alcohol, 4-nitrophenethyl alcohol, 2-(methyl sulfonyl)ethanol, 2-(phenyl sulfonyl)ethanol, 2-cyanoethanol, 2-(trimethylsilyl)ethanol, dimethylcarbamoyl chloride, diethylcarbamoyl chloride, ethylphenylcarbamoyl chloride, 1-pyrrolidinecarbonyl chloride, 4-morpholinecarbonyl chloride, diphenylcarbamoyl chloride and the like.

In some cases, the carbonyl-protecting group does not need to be particularly introduced. Moreover, in addition to the above-mentioned groups, a modified nucleic acid base (e.g., a 8-bromoadenyl group, a 8-bromoguanyl group, a 5-bromocytosyl group, a 5-iodocytosyl group, a 5-bromouracil group, a 5-iodouracil group, a 5-fluorouracil group, a 5-methylcytosyl group, a 8-oxoguanyl group, a hypoxanthinyl group etc.), which is a nucleic acid base substituted by any 1 to 3 substituents (e.g., a halogen atom, an alkyl group, an aralkyl group, an alkoxy group, an acyl group, an alkoxyalkyl group, a hydroxy group, an amino group, mono-alkylamino, dialkylamino, carboxy, cyano, nitro etc.) at any position(s), are also encompassed in the "nucleic acid base."

A substantially uncharged, phosphorus containing backbone in an oligonucleotide analog is one in which a majority of the subunit linkages, e.g., between 60-100%, are uncharged at physiological pH, and contain a single phosphorous atom. The analog contains between 5 and 40 subunits, typically about 8-25 subunits, and preferably about 12 to 25 monomeric subunits. The analog may have exact sequence complementarity to the target sequence or near complementarity, as defined below.

A "monomer" or "subunit" of an oligonucleotide analog refers to one nucleotide (or nucleotide analog) unit of the analog. The term may refer to the nucleotide unit with or without the attached inter-subunit linkage, although, when referring to a "charged subunit", the charge typically resides within the inter-subunit linkage (e.g. a phosphate or phosphorothioate linkage).

Figure 5:
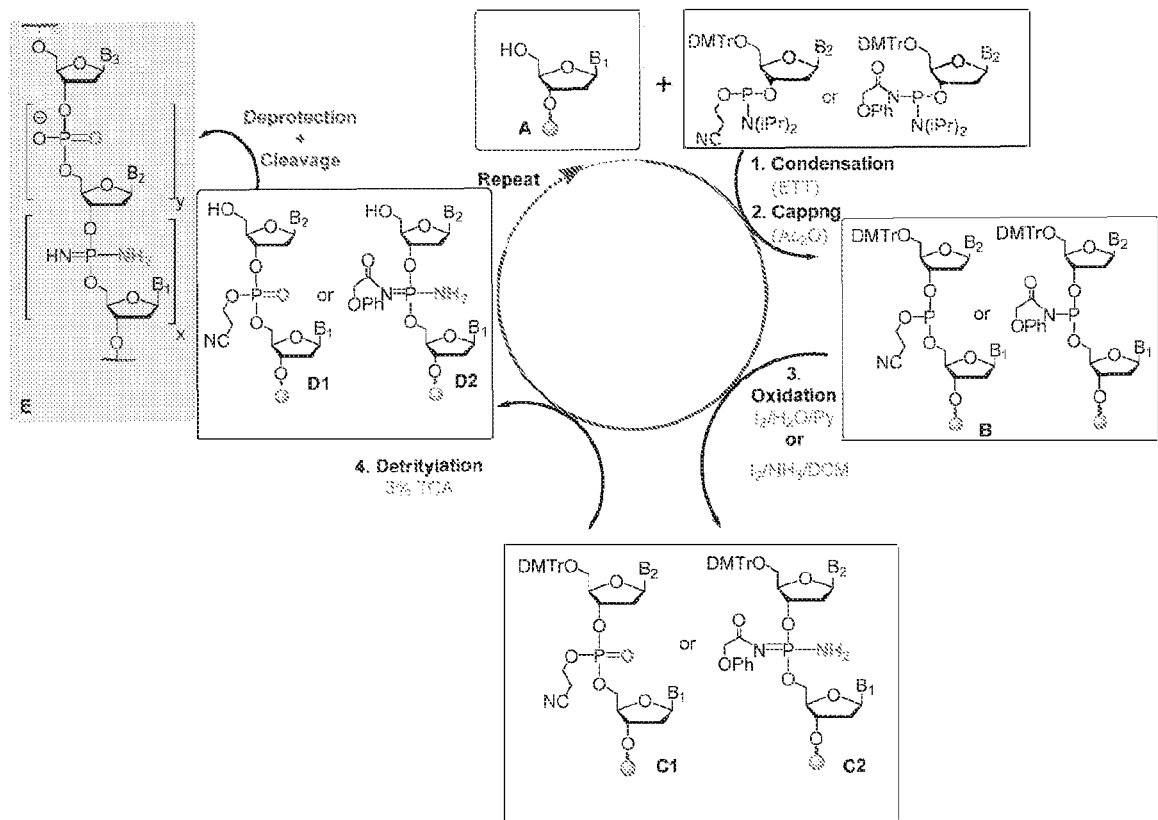
FIG. 5 shows an optimized solid-phase DNA synthesis cycle used to synthesize phosphoramidimidate DNA using a phenoxyacetamide protecting group approach.

An "oligonucleotide comprising a phosphoramidimidate internucleotide linkage" is an oligonucleotide analog composed of subunit structures of the form shown in FIG. 5, compound C2, where the structures are linked together by phosphorus-containing linkages, one to three atoms long, joining the 3' hydroxyl oxygen of one subunit to the 5' exocyclic oxygen of an adjacent subunit (wherein the "B" moieties are purine or pyrimidine base-pairing moieties effective to bind, by base-specific hydrogen bonding, to a base in a polynucleotide). The purine or pyrimidine base-pairing moiety is typically adenine, cytosine, guanine, uracil, or thymine.

The subunit and linkage shown in FIG. 5 are used for three-atom repeating-unit backbones, (where the six atoms include: the phosphorus atom, the atom (usually oxygen) linking the phosphorus atom to the 5' exocyclic carbon, and the 3' oxygen. In these structures, the phosphorus is covalently linked to nitrogen at both nonlinking internucleotide positions.

A preferred PIO comprises at least one linkage comprising phosphoramidimidate internucleotide linkage, referred to herein as a PIO, having a chemical structure:

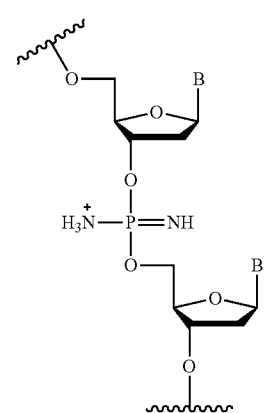

Wherein each 'B' moiety is purine or pyrimidine base-pairing moieties effective to bind, by base-specific hydrogen bonding, to a base in a polynucleotide.

The term "substituted", particularly with respect to an alkyl, alkoxy, thioalkoxy, or alkylamino group, refers to replacement of a hydrogen atom on carbon with a heteroatom-containing substituent, such as, for example, halogen, hydroxy, alkoxy, thiol, alkylthio, amino, alkylamino, imino, oxo (keto), nitro, cyano, or various acids or esters such as carboxylic, sulfonic, or phosphonic. It may also refer to replacement of a hydrogen atom on a heteroatom (such as an amine hydrogen) with an alkyl, carbonyl or other carbon containing group.

Sequences are described as "complementary" to one another when hybridization occurs in an antiparallel configuration. A double-stranded polynucleotide can be "complementary" to another polynucleotide. A targeting sequence may have "near" or "substantial" complementarity to the target sequence and still function for the purpose of the present invention. Preferably, the oligonucleotide analogs of this disclosure have at most one mismatch with the target sequence out of 10 nucleotides, and preferably at most one mismatch out of 20. Alternatively, the antisense oligomers of this disclosure have at least 90% sequence homology, and preferably at least 95% sequence homology, with the exemplary targeting sequences as designated herein. Thus, the oligomers made by the methods of this disclosure are particularly useful as therapeutic antisense molecules when administered to treat a disease state amenable to antisense therapy.

An oligonucleotide analog "specifically hybridizes" to a target polynucleotide if the oligomer hybridizes to the target under physiological conditions, with a Tm substantially greater than 45° C., preferably at least 50° C., and typically 60° C.-80° C., or higher. Such hybridization preferably corresponds to stringent hybridization conditions. At a given ionic strength and pH, the Tm is the temperature at which 50% of a target sequence hybridizes to a complementary polynucleotide. Again, such hybridization may occur with "near" or "substantial" complementarity of the antisense oligomer to the target sequence, as well as with exact complementarity.

A "nuclease-resistant" oligomeric molecule (oligomer) refers to one whose backbone is substantially resistant to nuclease cleavage, in non-hybridized or hybridized form; by common extracellular and intracellular nucleases in the body; that is, the oligomer shows little or no nuclease cleavage under normal nuclease conditions in the body to which the oligomer is exposed.

A "heteroduplex refers to a duplex between an oligonucleotide analog and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNAseH, which are capable of cutting double-stranded RNA/RNA or RNA/DNA complexes.

The oligonucleotide analogs of this disclosure preferably specifically bind to a target RNA sequence inside a cell. The base specificity of such binding is sequence specific. For example, a single-stranded polynucleotide can specifically bind to a single-stranded polynucleotide that is complementary in sequence.

These oligomers are positively charged and have the ability to be actively taken up by mammalian cells, and once taken up, form a duplex with target ssRNA with a Tm greater than about 50° C.

The following methods are useful for testing any given, substantially uncharged backbone for its ability to meet these requirements:

Active or Facilitated Uptake by Cells

The antisense oligomer may be taken up by host cells by facilitated or active transport across the host cell membrane if administered in free (non-complexed) form, or by an endocytotic mechanism if administered in complexed form.

In the case where the oligonucleotide is administered in free form, a small number of net charges, e.g., 1-2 for a 15- to 20-mer oligomer, can enhance cellular uptake of certain oligomers with substantially uncharged backbones. The charges may be carried on the oligomer itself, e.g., in the backbone linkages, or may be terminal charged-group appendages. Preferably, the number of charged linkages is no more than one charged linkage per four uncharged linkages. More preferably, the number is no more than one charged linkage per ten, or no more than one per twenty, uncharged linkages. In one embodiment, the oligomer is fully uncharged.

An oligomer may also contain both negatively and positively charged backbone linkages, as long as opposing charges are present in approximately equal number. Preferably, the oligomer does not include runs of more than 3-5 consecutive subunits of either charge.

In addition to being substantially or partially uncharged, an antisense oligonucleotide is preferably a substrate for a membrane transporter system (i.e., a membrane protein or proteins) capable of facilitating transport or actively transporting the oligomer across the cell membrane. This feature may be determined by one of a number of tests for oligomer interaction or cell uptake, as follows.

A first test assesses binding at cell surface receptors, by examining the ability of an oligomer compound to displace or be displaced by a selected charged oligomer on a cell surface. The cells are incubated with a given quantity of test oligomer, which is typically fluorescently labeled, at a final oligomer concentration of between about 10-300 nM. Shortly thereafter, e.g., 10-30 minutes (before significant internalization of the test oligomer can occur), the displacing compound is added, in incrementally increasing concentrations. If the test compound is able to bind to a cell surface receptor, the displacing compound will be observed to displace the test compound. If the displacing compound is shown to produce 50% displacement at a concentration of 10× the test compound concentration or less, the test compound is considered to bind at the same recognition site for the cell transport system as the displacing compound.

A second test measures cell transport, by examining the ability of the test compound to transport a labeled reporter, e.g., a fluorescence reporter, into cells. The cells are incubated in the presence of labeled test compound, added at a final concentration between about 10-300 nM. After incubation for 30-120 minutes, the cells are examined, e.g., by microscopy, for intracellular label. The presence of significant intracellular label is evidence that the test compound is transported by facilitated or active transport.

The antisense compound may also be administered in complexed form, where the complexing agent is typically a polymer, e.g., a cationic lipid, polypeptide, or non-biological cationic polymer, having an opposite charge to any net charge on the antisense compound. Methods of forming complexes, including bilayer complexes, between anionic oligonucleotides and cationic lipid or other polymer components, are well known. For example, the liposomal composition Lipofectin™, containing the cationic lipid DOTMA (N-[1-(2,3-dioleyloxy)propyl]-N,N,N-trimethylammonium chloride) and the neutral phospholipid DOPE (dioleyl phosphatidyl ethanolamine), is widely used. After administration, the complex is taken up by cells through an endocytotic mechanism, typically involving particle encapsulation in endosomal bodies.

The antisense compound may also be administered in conjugated form with an arginine-rich peptide linked to the 5' or 3' end of the antisense oligomer. The peptide is typically 8-16 amino acids and consists of a mixture of arginine, and other amino acids including phenyalanine and cysteine. Exposure of cells to the peptide conjugated oligomer results in enhanced intracellular uptake and delivery to the RNA target.

Alternatively, the requisite properties of oligomers with any given backbone can be confirmed by a simple in vivo test, in which a labeled compound is administered to an animal, and a body fluid sample, taken from the animal several hours after the oligomer is administered, is assayed for the presence of heteroduplex with target RNA.

Substantial Resistance to RNaseH

Two general mechanisms have been proposed to account for inhibition of expression by antisense oligonucleotides. In the first, a heteroduplex formed between the oligonucleotide and the viral RNA acts as a substrate for RNaseH, leading to cleavage of the target RNA. Oligonucleotides belonging, or proposed to belong, to this class include phosphorothioates, phosphotriesters, and phosphodiesters (unmodified "natural" oligonucleotides). Such compounds expose the viral RNA in an oligomer:RNA duplex structure to hydrolysis by RNaseH, and therefore loss of function.

A second class of oligonucleotide analogs, termed "steric blockers" or, alternatively, "RNaseH inactive" or "RNaseH resistant", have not been observed to act as a substrate for RNaseH, and are believed to act by sterically blocking target RNA nucleocytoplasmic transport, splicing, translation, or replication. This class includes methylphosphonates, morpholino oligonucleotides, peptide nucleic acids (PNA's), certain 2'-O-allyl or 2'-O-alkyl modified oligonucleotides, and N3'→P5' phosphoramidates.

A test oligomer can be assayed for its RNaseH resistance by forming an RNA:oligomer duplex with the test compound, then incubating the duplex with RNaseH under standard assay conditions. After exposure to RNaseH, the presence or absence of intact duplex can be monitored by gel electrophoresis or mass spectrometry.

In Vivo Uptake

Rapid tests exist for confirming that a given antisense oligomer type provides the required characteristics noted above, namely, high Tm, ability to be actively taken up by the host cells, and substantial resistance to RNaseH. This method is based on the discovery that a properly designed antisense compound will form a stable heteroduplex with the complementary portion of the target RNA when administered to a mammalian subject, and the heteroduplex subsequently appears in the urine (or other body fluid). Details of this method are given in U.S. patent application Publication No. 2001/0024783, the disclosure of which is incorporated herein by reference. Briefly, a test oligomer containing a backbone to be evaluated, having a base sequence targeted against a known RNA, is injected into an animal, e.g., mammalian subject. The antisense oligomer may be directed against any intracellular RNA, including a host RNA or the RNA of an infecting virus. Several hours (typically 8-72) after administration, the urine is assayed for the presence of the antisense-RNA heteroduplex. If heteroduplex is detected, the backbone is suitable for use in the antisense oligomers of the present invention.

The oligomer may be labeled, e.g. by a fluorescent or a radioactive tag, to facilitate subsequent analyses, if it is appropriate for the mammalian subject. The assay can be in any suitable solid-phase or fluid format. Generally, a solid-phase assay involves first binding the heteroduplex analyte to a solid-phase support, e.g., particles or a polymer or test-strip substrate, and detecting the presence/amount of heteroduplex bound. In a fluid-phase assay, the analyte sample is typically pretreated to remove interfering sample components. If the oligomer is labeled, the presence of the heteroduplex is confirmed by detecting the label tags. For non-labeled compounds, the heteroduplex may be detected by immunoassay if in solid phase format or by mass spectroscopy or other known methods if in solution or suspension format.

Exemplary Oligomer Backbones

A preferred oligomer structure employs phosphoramidimidate internucleotide linkages bearing base-pairing purine and/or pyrimidine moieties. Antisense oligomers, are detailed, for example, in U.S. Pat. Nos. 5,698,685; 5,217,866; 5,142,047; 5,034,506; 5,166,315; 5,185,444; 5,521,063; and 5,506,337, all of which are expressly incorporated by reference herein.

Important properties of these oligonucleotides include: the ability to be linked in an oligomeric form by stable phosphoramidimidate linkages; the ability to support a nucleotide base (e.g. adenine, cytosine, guanine or uracil) such that the polymer formed can hybridize with a complementary-base target nucleic acid, including target RNA, with high Tm, even with oligomers as short as 10-14 bases; the ability of the oligomer to be transported into mammalian cells; and the ability of the oligomer:RNA heteroduplex to resist RNAse degradation.

Backbone structures for antisense oligonucleotides of this disclosure include the morpholino subunit types shown in FIG. 5, linked by phosphoramidimidate linkage(s).

As noted above, substantially uncharged oligomers may advantageously include a number of charged linkages, e.g. up to about 1 per every 5 uncharged linkages, more preferably up to about 1 per every 10 uncharged linkages. Therefore, a number of uncharged linkages may also be incorporated into the oligomers.

Another aspect of this disclosure provides methods of oligonucleotides comprising phosphoramidimidate internucleotide linkages, comprising starting with a 5'-unprotected-2'-deoxyribonucleoside linked to a solid support, and reacting this 5'-unprotected-2'-deoxyribonucleoside with a synthon (i.e., monomer) having a chemical structure:

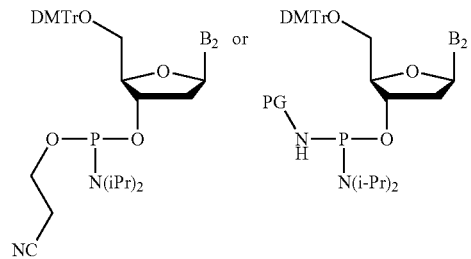

wherein each B2 is independently a nucleic acid base (adenosine, guanosine, uracil, thymine, cytosine, innosine), or a nucleic acid base protected with a silyl protecting group or an acid-labile or base-labile protecting group. This is preferably conducted in the presence of 5-(Ethylthio)-1H-tetrazole (ETT) and/or acetic anhydride (Ac$_2$O). The solid support may be polystyrene/CPG. This reaction forms an oligonucleotide having the chemical structure:

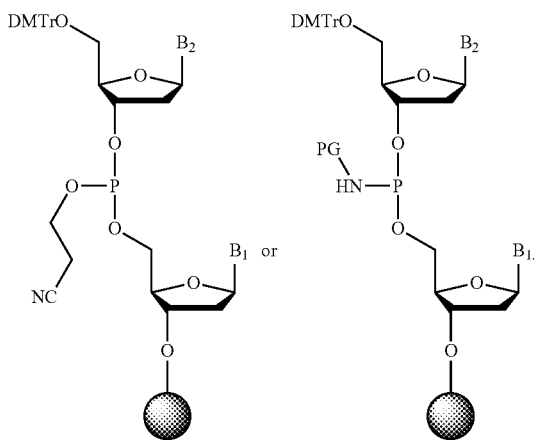

This oligonucleotide is then oxidized to form an oligonucleotide that may incorporate phosphoramidimidate internucleotide linkages having the chemical structure:

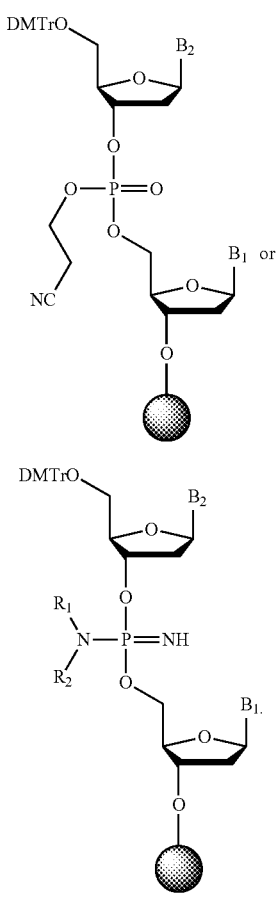

This oxidizing step may be conducted in a solution comprising iodine ($I_2$), ammonia ($NH_3$) and methylene chloride ($CH_2Cl_2$).

The oligonucleotide is then deprotected to remove the protecting group. The protecting group may be a 4,4'-Dimethoxytrityl, i.e., the deprotecting step may be detritylating in the presence of trichloroacetic acid and methylene chloride ($CH_2Cl_2$).

These steps (adding a synthon monomer through the steps of reacting, oxidizing and deprotecting) are repeated as desired to elongate the oligomer by adding monomers to the growing oligomer (growing step-wise from a dimer, to a trimer, to a tetramer, pentamer, hexamer, etc.).

The oligomers are then removed from the polystyrene support. This may be performed by contact the oligomer with a solution comprising ammonium hydroxide and ethylene diamine.

These repetitive monomer additions to the oligomer may be performed on a common commercial DNA synthesizer, thereby greatly enhancing the efficiency and speed of the synthesis in a cost-effective manner.

Exemplary synthon monomers for use in the synthesis methods of this disclosure include phosphoramidimidate having a chemical structure:

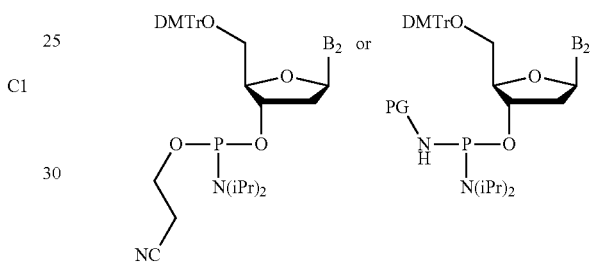

Wherein B2 is may be a silyl protecting group, or acid labile or base labile protecting group, such as:

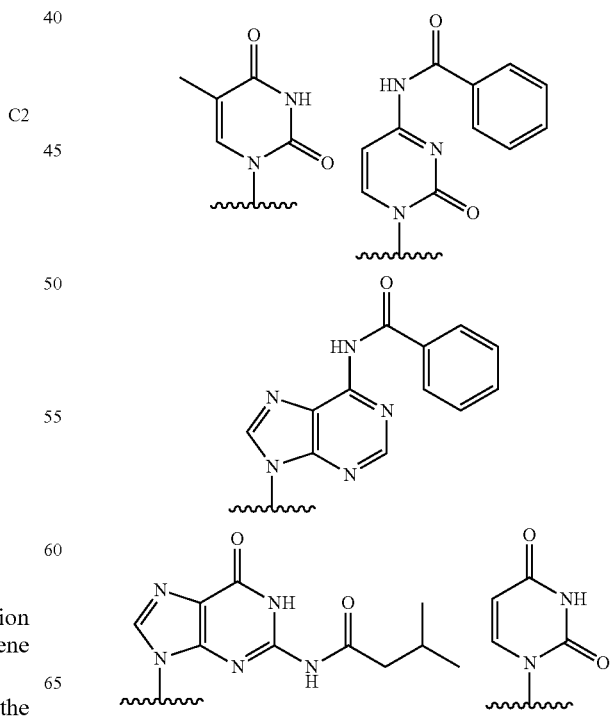

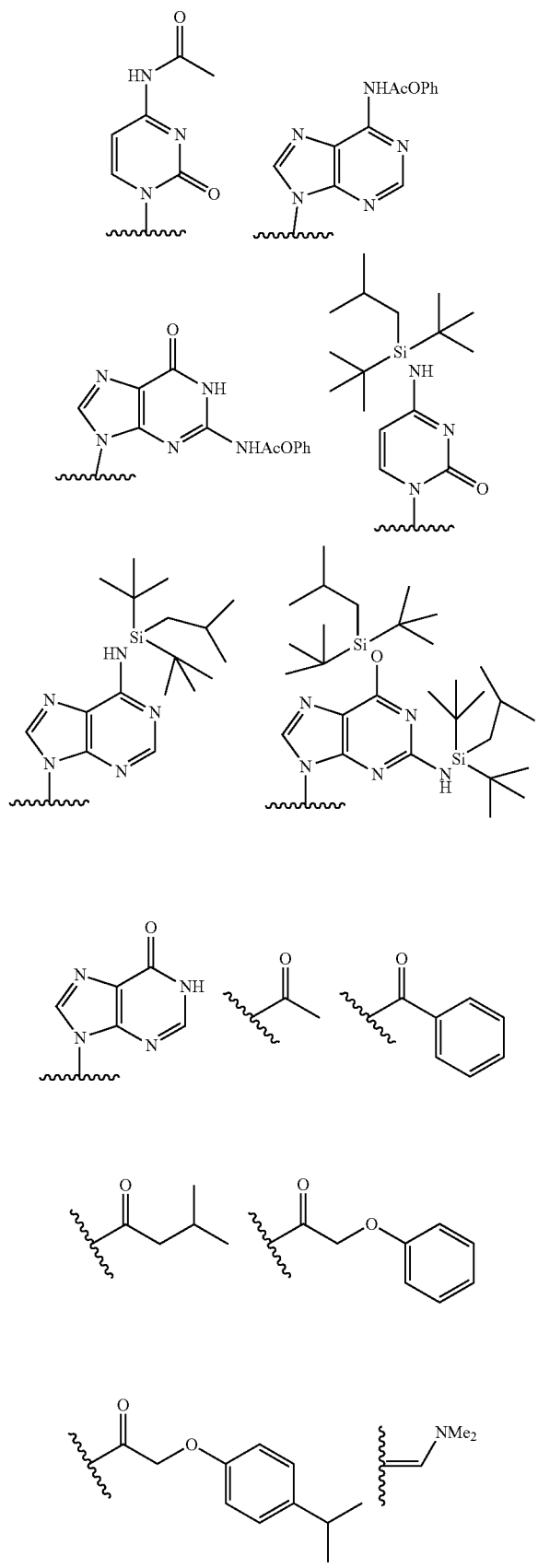
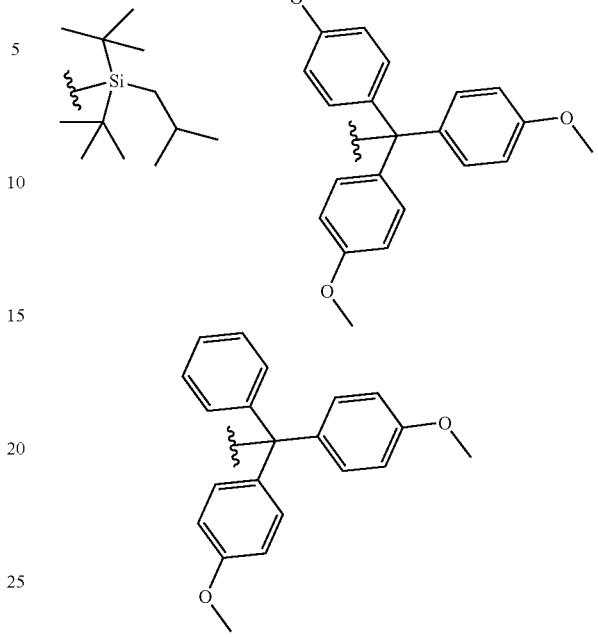

Each publication or patent cited herein is incorporated herein by reference in its entirety.

The disclosure now being generally described will be more readily understood by reference to the following examples, which are included merely for the purposes of illustration of certain aspects of the embodiments of the present disclosure. The examples are not intended to limit the disclosure, as one of skill in the art would recognize from the above teachings and the following examples that other techniques and methods can satisfy the claims and can be employed without departing from the scope of the claimed disclosure.

EXAMPLES

Example 1

Phenoxyacetyl Protecting Group Validation

The inventors have developed successful methods of using phenoxyacetamide for the synthesis of phosphoramidimidate DNA. Phenoxyacetyl has been used to protect the exocyclic amines of the nucleobases. For this application it showed complete deprotection under mild conditions: 29% ammonia at room temperature in less than four hours. The ability to remove the phenoxyacetyl protecting group under mild conditions was tested for the synthesis of phosphoramidimidate DNA using an approach outlined previously with the cyanoethyl amide protecting group.

As proof of concept, a 2'-deoxythymidine dinucleotide was synthesized with the linking phosphate containing a phosphoramidimidate, with phenoxyacetamide protection (FIG. 1). The usual 5' DMT was replaced with a base labile levulinoyl group ("Lev"). This was considered necessary so that acid lability studies on the phenoxyacetamide completed without interference from the carbocation as generated by cleavage of the DMT group. Phosphorous (III) dinucleotide compound XXX was oxidized to the corresponding phosphorous (V) dinucleotide using 0.25 M $NH_3$/ 0.02M $I_2$ in dioxane.

The synthesis started by condensing bis(diisopropylamino) chlorophosphine with phenoxyacetamide to generate bis(diisopropylamino) phenoxyacetamidophosphane (X) in 71% yield. Compound X was then condensed with 5'-O-levulinoyl-2'-deoxythymidine in the presence of ETT to yield XX in 84% yield. The next step was condensation of XX with 3'-O-acetylthymidine to yield the dinucleotide XXX in 82% yield. Finally, this phosphoramidite was oxidized with solution of 0.02 M $I_2$/0.25M $NH_3$ in dioxane to yield the phenoxyacetamide phosphoramidimidate (XXXXX, 88% yield).

The stability of the dinucleotide compound (XXXX) was examined with respect to the following reagents used in the solid phase synthesis cycle:
 1. 3% Trichloroacetic acid in dichloromethane.
 2. Cap mixture A: 10% Acetic Anhydride, 10% Pyridine, 80% THF.
 3. Cap mixture B: 1-Methylimidazole in THF.
 4. Tert-butyl peroxide solution: 0.5 tert-butyl peroxide solution M in DCM.

In each experiment, 50 mg of the dinucleotide and the appropriate reagent were added to a NMR tube. The $^{31}P$ NMR was monitored to test for degradation by the formation of new peaks and/or decreased intensity of the starting material peak. Cap mixture A, cap mixture B, and t-butyl peroxide showed no degradation within 12 hours. The protected dinucleotide phosphoramidimidate showed 15% degradation after 24 hours with 3% trichloroacetic acid. Thus, the phosphoramidimidate dinucleotide, when protected by phenoxyacetyl, is as acid stable as the cyanoethylamide protecting group used previously.

Example 2

DNA Solid Phase Phosphoramidimidate Synthesis Using

Phenoxyacetyl Protecting Group

Figure 2:
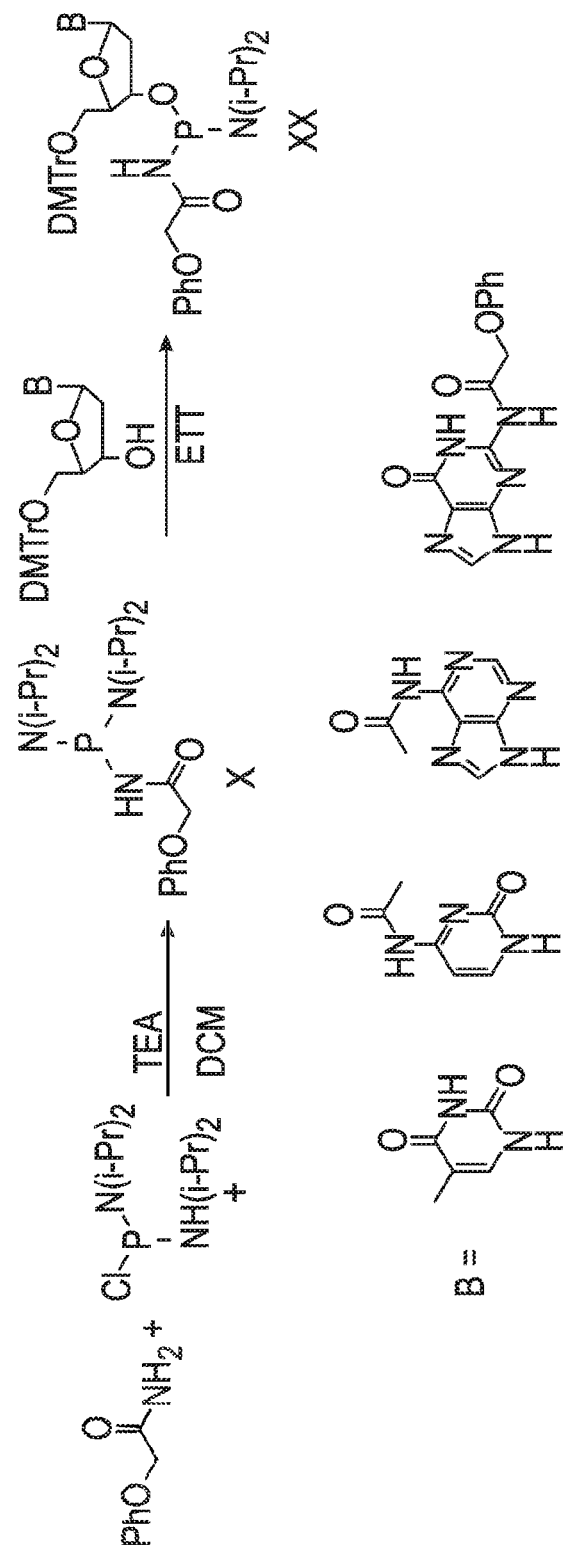
FIG. 2 is a synthesis scheme for the chemical synthon compounds XX-XXXXX used as precursors in the solid phase DNA synthesis cycle.

Because cyanoacetamide and phenoxyacetamide have similar reactivity towards reagents used in sold phase DNA synthesis cycles and reactivity towards activation with ETT, the same synthetic procedures used for the cyanoacetamide protecting group were used with the phenoxyacetamide synthesis approach. The preparation started by dissolving phenoxyacetamide in DCM followed by adding 1.1 equivalents of triethylamine and stirred for 15 minutes. 0.9 equivalents of bis(diisopropylamino)-chlorophosphine was added and the reaction monitored by $^{31}P$ NMR. The disappearance of the 141 ppm $^{31}P$ NMR peak indicated complete consumption of the starting material, while the appearance of the new peak at 112 ppm, indicated the formation of the desired phosphoramidite. 1.0 equivalents of 5'-O-DMT-2'-deoxythymidine and 0.9 equivalents of ETT were added to the reaction mixture and the reaction monitored by TLC until all the 5'-O-DMT-2'-deoxythymidine was consumed (FIG. 2).

The same synthetic procedure was used for preparing 5'-O-DMT-N-acetyl-2'-deoxyadenosine, 5'-O-DMT-N-acetyl-2'-deoxycytidine, and 5'-O-DMT-N-phenoxyacetyl-2'-deoxyguanosine. All compounds (XX-XXXX) were confirmed by 2D NMR, 13C NMR, $^{31}P$ NMR and mass spectrometry. The preparation of these synthons generated both diastereomers as evidenced by $^{31}P$ and TLC. However, the diastereomers proved inseparable by silica column chromatography under multiple solvent conditions.

To validate compatibility of these synthons (XX-XXXX) with solid phase DNA synthesis, DNAs containing phenoxyacetamide phosphoramidimidate internucleotide linkages at variable positions were synthesized using the standard solid phase synthesis cycle. For simplicity, synthon XX was chosen for oligonucleotide synthesis. A T12 oligonucleotide containing one modification located at the final internucleotide linkage at the 5'-end of the 12 mer oligonucleotide was synthesized first. In this synthesis scheme, exposure to different reagents during the solid phase cycle was minimized. The final 5' DMT protecting group was left on the oligonucleotide because this group shifts the final polynucleotide away from failure sequences and gives a clearer image on the HPLC profile for evaluating the synthesis products and coupling efficiency. After cleavage from the solid support, using portions of the crude synthesis mixture were analyzed by HPLC. Synthesis of several T15 oligomers and analysis of the data from these experiments resulted in the following modifications to the standard solid phase phosphoramidite synthesis protocol:

1) Condensation Step: The concentration of phenoxyacetyl phosphoramidite was increased from 0.1M to 0.2M. This change increased the product yield and decreased the amount of failure sequences. Using ETT as the activator and extending the condensation time to 15 minutes increased the product yield and decreased the amount of failure sequences too. Introduction of the monomers twice to the reaction column did not change the coupling yield.
2) Oxidation: The standard oxidizing solution consisting of $I_2/H_2O$/Pyridine was used to convert phosphite triester to phosphate when the regular phosphate linkage was incorporated into an oligonucleotide. The use of peroxide oxidizing solution had no beneficial effect.
3) Iodine/ammonia oxidation: Anhydrous ammonia and $I_2$ dissolved in DCM was used to convert the phenoxyacetyl protected phosphoramidite into phosphoramidimidate. This oxidizing solution was initially loaded into the column for 15 seconds which was enough time to fill the column. The reaction was then allowed to proceed for 240 seconds. The column was flashed with argon for 10 seconds to remove the oxidizing reagents. A new oxidation solution was then loaded onto the column and the second incubation time was 120 seconds.

To further test the synthesis, thymidine containing polynucleotides 12 to 21 residues in length and having two to four modifications at variable positions were synthesized, the reaction mixtures were analyzed by HPLC, and the product characterized by $^{31}P$ NMR and mass spectrometry. HPLC profiles of crude reaction mixtures produced from the modified solid phase DNA synthesis cycles were compared with the standard DNA synthesis cycle crude reaction mixtures. The targeted product peak appeared at retention time 24 and failure sequences at 10-14 minute. Sequences of the thymidine containing polynucleotides produced were:
 A) 5'-DMT-TTTTTTTTTTTTTTTTTTTTT;
 B) 5'-DMT-TT*TTTT*TTTTT*T;
 C) 5'-DMT-TT*TTTTTTTT*TTTTTTTTT*T;
 D) 5'-DMT-TTTTTTTTTTTTTTTT*TT*TT*T;
 wherein *=phosphoramidimidate modifications.

Example 3

Phenoxyacetamide Deprotection Study Using HPLC and Mass Spectrometry

Although phenoxyacetamide can be removed in 1 hour with aqueous ammonia when used to protect the exocyclic amines of nucleobases, cytosine, adenine, and guanine, it was more difficult to remove when used as the phenoxyacetyl protecting group on the phosphoramidimidate internucleotide linkage. Therefore, several deprotection procedures were evaluated for removal of the phenoxyacetamide from the phosphoramidimidate. These test procedures included varying the basic conditions used for deprotection, time, temperature, and hydrous verses anhydrous conditions. The specific reagents and conditions included: aqueous ammonia, anhydrous ammonia in dioxane, 1:1 anhydrous ammonia/toluene, 1:1 anhydrous ammonia/ethylenediamine, 1:1 ethylenediamine/toluene, aqueous ammonia with 10% ethylene diamine, DBU, aqueous ammonia with 10% 2-pyrrolidone, aqueous ammonia with 10% pyrrolidine, aqueous ammonia and 10% ethylenediamine.

The study was performed on 2'-deoxyoligonucleotide containing 22 nucleotides having a mixed combination of nucleobases including 3 phosphoramidimidate internucleotide linkages per oligomer. Each synthesized oligomer, while still attached to CPG was divided into two parts; one was cleaved from CPG using 30% aqueous ammonia for 1 hour at room temperature, the ammonia was removed and the oligomers were redissolved in water. These conditions did not remove the phenoxyacetamide protecting group. A sample of this aqueous solution was injected in the HPLC to evaluate the quality of the total product mixture. The second half was dissolved in the appropriate test solution and injected under the desired conditions. Solvent was removed, the sample was redissolved in water and injected into the HPLC. The HPLC profiles of these two samples were then compared to evaluate.

The best deprotection of phenoxyacetamide was 0.5 mL ethylenediamine at room temperature for 15 minutes followed by 0.5 mL of 0.5 M anhydrous ammonia in dioxane for 24 hours at 45° C. Increasing the temperature to 55° C. of this reaction mixture generated shorter oligos due to phosphorous bond breakage. This optimized protocol was also served to cleave the 2'-deoxyoligonucleotide from the solid support and remove the nucleobase protecting groups from cytosine, guanine and adenine.

All samples were analyzed by mass spectrometry in order to confirm complete deprotection and generation of the desired phosphoramidimidate. $^{31}$P NMR provided further evidence because the protected phosphoramidimidate appears at 10 ppm and the deprotected phosphoramidimidate appears at 12 ppm when deuterated water is used as the solvent.

Example 4

Phenoxyacetamide Base Deprotection Study Using $^{31}$P NMR

Because the chemical shift of the unprotected phosphoramidimidate (12 ppm) was at higher resonance than the phenoxyacetamide protected linkage (10 ppm), an additional study was carried out to confirm this assignment. A 2'-deoxyoligonucleotide containing 22 internucleotide linkages in which three were phenoxyacetamide phosphoramidimidate linkages, was prepared on a support in which the oligomer was linked by hydroquinone-O,O'-diacetic acid, (Q-linker) rather than the traditional succinyl linker which takes about 1 hour in aqueous ammonia. With this support (Q-linker), the oligomer could be cleaved in 5 minutes using 1 mL of 0.5 M K$_2$CO$_3$ in methanol which insured that phenoxyacetamide protection remained intact. Following removal of methanol by evaporation, the sample was redissolved in 1 mL of 2M ammonium acetate buffer at pH 7 and 0.1 mL deuterated water.

To further explore this result, the exposure of the oligo to the basic conditions was minimized and the location of the appearance of the peaks on the $^{31}$P NMR was determined. The oligo could be cleaved from the solid support in 5 minutes using K$_2$CO$_3$ in methanol. $^{31}$P NMR was acquired and it confirmed the chemical shifts. $^{31}$P NMR spectrum for T-22 polynucleotides containing the three phosphoramidimidate internucleotide linkages (and a 5'-Oxygen protected with DMT) showed the natural phosphate internucleotide linkage appeared at −1 ppm, and two other peaks appeared at 10 and 12 ppm. The major peak at 10 ppm corresponds to the intact phenoxyacetamide phosphoramidimidate and the smaller peak at 12 ppm corresponds to the deprotected phosphoramidimidate internucleotide linkage. This result was confirmed by mass spectrometry, which showed a peak at 1731.3235 corresponding to the oligonucleotide in which all three phosphoramidimidate linkages had been deprotected, and peaks at 1764.8497, 1798.3455 and 1831.8571 corresponding to oligonucleotides in which 2, 1, or none of the phosphoramidimidate linkages had been deprotected, respectively.

Example 5

Modification and Deprotection Studies

Figure 3:
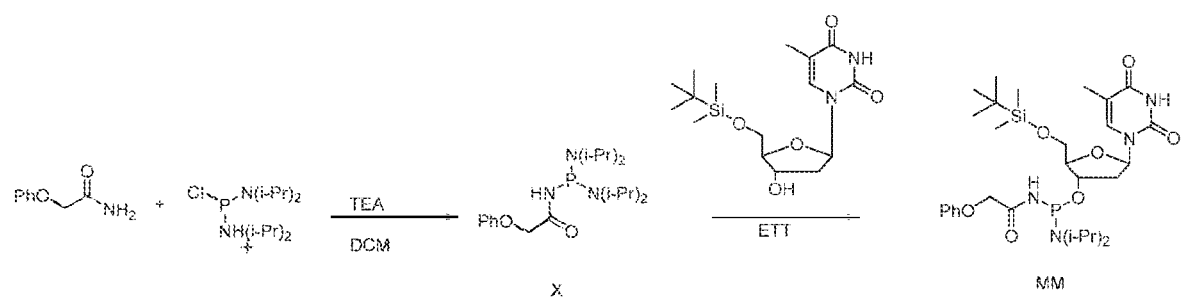
FIG. 3 is a synthesis scheme for compound MM phosphordiamidite which is 5' protected with a t-butyldimethylsilyl group.

Phosphoramidimidate is stable towards acids as long as it is in the amide form, but when the amide protecting group is removed it is acid sensitive at pH lower than 4. Because it is desirable to retain the 5' DMT group during RP-HPLC in order to separate the desired product away from failure sequences which are free of the DMT group, a new procedure was needed for removal of this group as the last synthesis step or identifying a new 5' protecting group. The traditional method of removing DMT is stirring for 1 hour at room temperature in 80% aqueous acetic acid. Unfortunately, these acidic conditions caused degradation of the phosphoramidimidate oligonucleotide. The inventors therefore investigated the use of the t-butyldimethylsilyl group as a solution for dimethoxytrityl because both are hydrophobic and therefore useful in reverse phase HPLC. Additionally, silyl protecting groups can be removed using fluoride solution under nonacidic conditions. Commercially available 5'-O-(t-butyldimethylsilyl)-2'-deoxythymidine was used to synthesize the precursor for synthesis of phosphoramidimidate DNA (depicted in in FIG. 3).

The structure of synthon MM (FIG. 3) was confirmed by $^{31}$P NMR, $^{13}$C NMR, $^{1}$H NMR, and mass spectrometry. Synthon MM was used in the solid phase cycle but unfortunately this compound was found to be unacceptable as overall synthesis yields were low and numerous failure sequences were observed.

Figure 4:
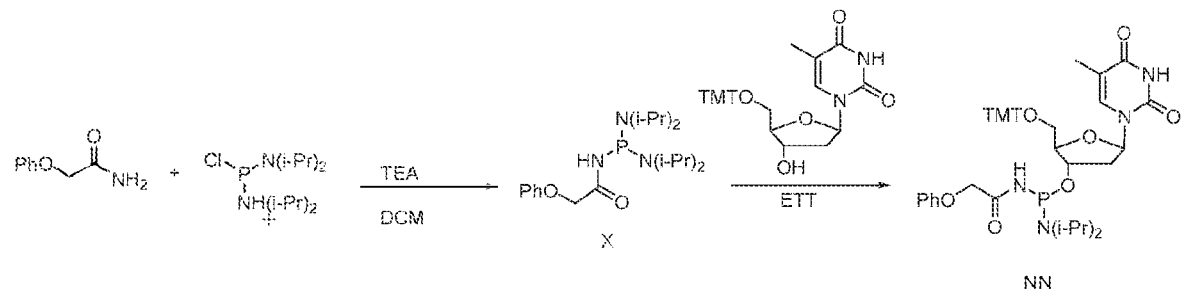
FIG. 4 is a synthesis scheme for compound NN phosphordiamidite which is 5' protected with a trimethoxytrityl group.

Studies utilizing the trimethoxytrityl (TMT) as a 5' protecting group proved to be a successful choice. This group has the same protecting functionality and lipophilicity as DMT but is acid labile at a higher pH. These advantages suggested synthesis of an oligonucleotide 5'-protected with TMT and containing phosphoramidimidate internucleotide linkages. The same synthetic path was used to prepare the precursors for phosphoramidimidate solid phase cycle except that 5'-O-DMT-2'-deoxythymidine was replaced with 5'-O-DMT-2'-deoxythymidine (FIG. 4).

To further test the TMT approach, a 2'-deoxyoligonucleotide containing six phosphoramidimidate internucleotide linkages with a last 5'-TMT thymidine nucleobase was synthesized (5'-TMT-T*GT*AAA*CCAT*GAT*GTGCTGCT*A). This deoxyoligonucleotide was cleaved from the solid support and the phenoxyacetyl group was removed and purified using reverse phase HPLC. Incubating the oligo at pH 5 for 12 hours at room temperature deprotected the 5' end and generated the desired oligo.

Example 6

Optimized Cleavage and Purification Procedure

Using these optimized procedures for synthesizing phosphoramidimidate DNA, 2'-deoxyoligonucleotides 15 to 22 nucleotides in length with 3 to 14 phenoxyacetamide phosphoramidimidate internucleotide linkages were synthesized as depicted in FIG. 5.

The sequential optimized cleavage and purification procedure is as follows:
1. Cleave the 2'-deoxyoligonucleotide from the solid support and simultaneously remove the nucleobase and the phenoxyacetyl protecting groups using 1:1 ethylenediamine:0.5M NH₃ in dioxane (24 hours at 45° C.);
2. Using prep-HPLC the product 2'-deoxyoligonucleotide containing a 5'-TMT was separated from side products. This was possible because the hydrophobic product has a longer retention time than side-products lacking the TMT group.
3. Incubate the purified oligo in 1:1:1 water:acetic acid: tetramethylethylenediamine at pH 5 for 12 hours at room temperature. These conditions remove the TMT group without generating 2'-deoxyoligonucleotide degradation products.
4. Neutralize the reaction solution using 1M triethylammonium bicarbonate
5. Purify the product 2'-deoxyoligonucleotide using prep-RP-HPLC.

The synthesized 2'-deoxyoligonucleotides containing 3-14 phosphoramidimidate modifications at various positions are listed in the following table:
2'-Deoxyoligonucleotide sequences containing phosphoramidimidate modification used for molecular weight analysis, NMR, Tm and biological activity studies (* phosphoramidimidate linkage; 6-FAM-P(S): 5'-fluorescein thiophosphoramidate.)

| No. | Structure |
| --- | --- |
| ODN1 | DMT-T*TTTTTTTT*T[-2] |
| ODN1 | DMT-TTT*TTT*TTT*TTT[-3] |
| ODN1 | T12-2M-DMTon |
| ODN1 | DMT-TTTTT*TTTTTT*TTTTTT*TTTT[-4] |
| ODN1 | DMT-AAAAT*AAAAAT*AAAAAT*AAAA[-4] |
| ODN1 | DMT-AAAAA*AAAAAA*AAAAAA* AAAA[-3] |
| ODN2 | DMT-TGTA*AA*CCA*TGA*TGTGCTGCTA[-3] |
| ODN3 | DMT-TGT*AAACCAT*GAT*GT*GCTGCTA[-3] |
| ODN4 | DMT-TGT*AAA*CCA*TGAT*GTGCT*GCTA[-3] |
| ODN5 | DMT-T*GTA*AACCA*TGATGTGCTGCT*A[-3] |
| ODN6 | DMT-TG*TAAACCATG*ATGTGC*TGC*TA[-3] |
| ODN7 | DMT-TG*TAAACC*ATG*ATGTGC*TGC*TA[-3] |
| ODN8 | DMT-TG*TAAACC*ATG*ATG*TGC*TGC*TA[-3] |
| ODN9 | DMT-TG*TAA*ACC*ATG*ATG*TGC*TGC*TA[-3] |
| ODN10 | DMT-TGT*AAA*CCA*TGA*TGT*GCT*GCT*A[-3] |
| ODNC | TGTAAAC*C*ATGATGTGC*TGC*TA |
| L-6-5 | T*GT*AAACC*AT*GAT*GTGCTGCT*A[-4] |
| L-6-6 | T*GTA*AA*CCAT*GA*TGTGCTGCT*A[-4] |
| L-5-7 | T*GT*AAACC*ATGAT*GTGCTGCT*A[-4] |
| T-1 | T*GT*AA*ACCA*TGAT*GTGCTGCT*A |
| CT-1 | TAGC*AGC*ACATC*ATG*GTTTACA |
| T-2 | T*GT*AAA*CCAT*GAT*GTGCTGCT*A |
| CT2- | TAGC*AGC*ACAT*CAT*GGTT*TACA |
| T-4 | TA*CT*GA*GA*GA*CA*CT*GA*TT*CT*GA*A |
| CT-4 | TT*CA*GA*AT*CA*GT*GT*CT*CT*CA*GT*A |
| F-4-1 | 6-FAM-P(S)- TG*TAAACC*ATGAT*GTGCTGCT*A[-4] |
| F-7-2 | 6-FAM-P(S)- T*GTA*AA*CCAT*GA*TGT*GCTGCT*A[-4] |
| F-6-3 | 6-FAM-P(S)- T*GT*AAACC*ATG*ATGT*GCTGCT*A |
| NTC-1 | 6-FAM-P(S)- C*TAGCC*ATG*ATGT*GTGCTGCT*A |
| F-5-5 | 6-FAM-P(S)- TGT*AAACC*AT*GAT*GTGCTGCT*A |
| F-6-6 | 6-FAM-P(S)- T*GTA*AA*CCAT*GA*TGTGCTGCT*A |
| F-5-7 | 6-FAM-P(S)- T*GT*AAACC*ATGAT*GTGCTGCT*A |
| Si | |

These 2'-deoxyoligonucleotides were used for several experiments including thermal denaturation and biological activity studies.

Example 7

Phosphoramidimidate Positive Charge

Because alkylammonium ions (RNH₃⁺) have a PKa range between 10-11, the alkyl amine attached to the phosphorus is expected to be protonated at pH lower than 10. This was observed during liquid chromatography mass spectrometry (LC-MS) analysis using ammonium acetate buffer (pH 7). An extra hydrogen atom was added to the oligonucleotide exact mass per modification which indicates this extra hydrogen came from protonation. To prove that the phosphoramidimidate internucleotide linkage has a positive charge, a gel mobility comparison study was performed to compare between three types of DNA internucleotide linkages that have different charges. The natural DNA phosphate has a negative charge, the phosphoramidate has a neutral charge, and the phosphoramidimidate is expected to have positive charge. The inventors synthesized and tested 12-mer oligonucleotides with 3 out of 11 phosphate linkages modified with a phosphoramidate or phosphoramidimidate, in addition to the natural phosphate oligonucleotide. Thus, the overall charge for oligonucleotides containing all-natural phosphate linkages was −11 (ODN1 in FIG. 6), for the oligonucleotide containing 3 phosphoramidate linkages was −8 (ODN2: in FIG. 6), and for the oligonucleotide containing 3 phosphoramidimidate linkages was −5 (ODN3: in FIG. 6).

Figure 6:
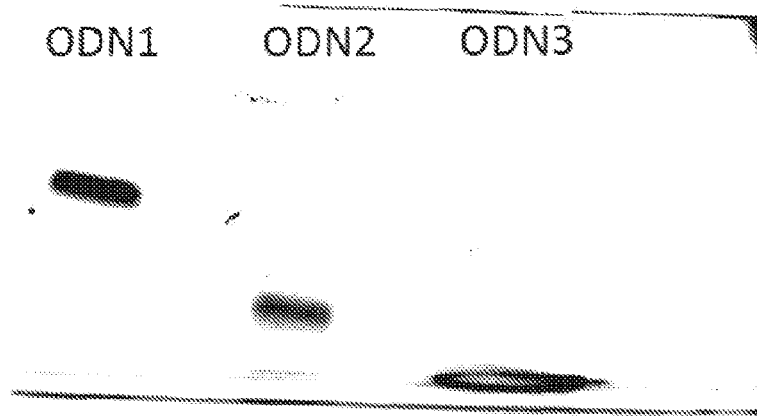
FIG. 6 shows a denaturing polyacrylamide gel electrophoresis for three deoxyoligonucleotides displaying differences in mobility despite close molecular weight, due to the differences in the overall charges.

In FIG. 6: ODN1 is d(TTTTTTTTTTT);

ODN2 is d(T #TTTTT #TTTTT #T), where # is phosphoramidate linkage

ODN3 is d(T*TTTTT*TTTTT*T), where * is phosphoramidimidate linkage).

As expected, these three oligonucleotides showed different mobility on denaturing polyacrylamide gel using electrophoresis (FIG. 6) despite being close in molecular weight due the difference in the overall charge. This observation confirms that the phosphoramidimidate internucleotide linkage is positively charged at pH 8 which is consistent with the LC-MS results and detection of extra hydrogen atom per modification.

Example 8

Thermal Denaturation Studies

The ability of an oligonucleotide to bind to its target is an important parameter for certain biological activities. For example, various modified DNAs may have applications in antisense or antagomir therapy, but their utility is significantly impacted by the ability of the oligonucleotides to recognized and bind to target RNA. To study the binding ability of the phosphoramidimidate DNAs to complimentary DNA and RNA, thermal denaturation studies were carried out by measuring the Tm values for duplexes and observing the effects of phosphoramidimidate modification on duplex formation as the number of modifications is increased. The procedure includes forming duplexes having phosphoramidimidate DNA modifications in one strand that is complementary to DNA or RNA. The modifications are introduced either in one strand or in both strands, but not opposing each other. Tm values are then measured as a function of the number of phosphoramidimidate modifications in each oligonucleotide.

2'-Deoxyoligonucleotides were mixed with the cDNA and cRNA in a 1:1 ratio (final concentration 1.0 μM of duplex) in solutions of 1.0 M NaCl/0.01 M Na$_2$HPO$_4$, 0.10 M NaCl/0.01 M Na$_2$HPO$_4$, 0.01M NaCl/0.01 M Na$_2$HPO$_4$ at pH 7.3. The samples were denatured at 90° C. for 3 minutes and cooled to 25° C. They were then heated at a rate of 1° C./min, and absorbance was recorded. Melting temperatures were taken as the temperature of half dissociation and were obtained from the first derivative plots. Tm values for unmodified phosphate DNA and RNA of the same sequence with cDNA were determined for comparison.

Tm's were measured for duplexes having variable numbers of phosphoramidimidate modifications and locations within the 2'-deoxyoligonucleotides in order to determine the effect of modification on binding. On average, it was found that the Tm depression was 0.5° C. per modification at 100 mM or 10 mM NaCl and 1° C. per modification at 1.0 M NaCl. Additionally, Tm measurements were carried out with duplexes having phosphoramidite linkages. The Tm results summarized in the following tables:

Melting temperature of duplex X/X', X/cS, S/X' and S/cS

| Duplex | Number of modifications first strand | Number of modifications complementary strand | Tm | ΔTm** | ΔTm/total number of modifications |
|---|---|---|---|---|---|
| X/X' # | 5 | 5 | 52.12 | 2.95 | 0.30 |
| X/cS # | 5 | 0 | 54.07 | 1.0 | 0.20 |
| S/X' # | 0 | 5 | 54.12 | 0.95 | 0.19 |
| S/cS # | 0 | 0 | 55.07 | 0 | 0 |
| X/X' ## | 5 | 5 | 66.22 | 8.9 | 0.89 |
| X/cS ## | 5 | 0 | 71.17 | 3.95 | 0.79 |
| S/X' ## | 0 | 5 | 70.17 | 4.95 | 0.99 |
| S/cS ## | 0 | 0 | 75.12 | 0 | 0 |

X = d(5'-TGTp*AAp*ACCAp*TGATp*GTGCTGCTp*A);
X' = d(5'-TAGCp*AGCp*ACATCp*ATGp*GTTTACp*A);
S = d(5'-TGTAAACCATGATGTGCTGCTA);
cS = d(5'-TAGCAGCACATCATGGTTTACA);
10 mM NaCl/10 mM Na$_2$HPO$_4$;
1M NaCl/10 mM Na$_2$HPO$_4$;
*= phosphoramidimidate;
**ΔTm = Tm for standard DNA − observed Tm.

Melting temperature of duplex X/X', X/cS, S/X' and S/cS;

| Duplex | Number of modifications first strand | Number of modifications complementary strand | Tm (° C.) | ΔTm** (° C.) | ΔTm/total number of modifications |
|---|---|---|---|---|---|
| X/X' # | 11 | 11 | 36.52 | 15.6 | 0.7 |
| X/cS # | 11 | 0 | 44.52 | 7.6 | 0.69 |
| S/X' # | 0 | 11 | 46.57 | 5.55 | 0.50 |
| S/cS # | 0 | 0 | 52.12 | 0 | 0 |
| X/X' ## | 11 | 11 | 46.12 | 16.9 | 0.77 |
| X/cS ## | 11 | 0 | 54.02 | 9 | 0.81 |
| S/X' ## | 0 | 11 | 55.07 | 7.95 | 0.73 |
| S/cS ## | 0 | 0 | 63.02 | 0 | 0 |

X = d(5'-TA*CT*GA*GA*GA*CA*CT*GA*TT*CT*GA*A);
X' = d(5'-TT*CA*GA*AT*CA*GT*GT*CT*CT*CA*GT*A);
S = d(5'-TACTGAGAGACACTGATTCTGAA);
cS = d(5'-TTCAGAATCAGTGTCTCTCAGTA);
10 mM NaCl/10 mM Na$_2$HPO$_4$;
100 mM NaCl/10 mM Na$_2$HPO$_4$;
*= phosphoramidimidate;
**ΔTm = Tm for standard DNA − observed Tm.

Example 9

Enzymatic Studies Against Snake Venom Phosphodiesterase Exonuclease (SVPDE)

To evaluate the relative exonuclease susceptibility of phosphoramidimidate modified DNA, selected 2'-deoxynucleotides were tested for stability against snake venom phosphodiesterase (SVPDE, 3'-exonuclease). A 2'-deoxyolionuceotide of thymidine 10 mer was synthesized to contain two phosphoramidimidate linkages—one at the 5'- and one at the 3' end (ODN29). An unmodified polythymidylate DNA (10-mer) was used as the control. A sample of the oligomer (2 OD) was incubated at 37° C. with 150 μL of 100 mM Tris-HCl buffer (pH 9.0), 10 mM MgCl2, (2.5 μg) SVPDE with the total volume made up to 200 μL. Aliquots were removed at different time points, quenched by the addition of 1.0 M EDTA and stored in dry ice until analyzed by analytical RP-HPLCLC.

Time-dependent enzymatic exonuclease degradation of ODN1 (5'-DMT-TTTTTTTTTT) and ODN2 (5'-DMT-T*TT TTT TTT*T where * is phosphoramidimidate linkage) was tested by treating these ODNs with SVPDE, and aliquots of the reaction mixture were analyzed by RP-HPLC at different time points (0, 30, 60 min, 0, 1, and 12 hours). Oligonucleotide degradation from the 3' end was indicated by appearance of mono-nucleotide peaks using the reverse phase HPLC (RF-HPLC) on retention time around 6.

When a 2'-deoxyoligonucleotide was incubated with SVPDE, it started degrading the oligonucleotide from the 3' end and generated a mono-nucleotide which appears using the reverse phase HPLC (RF-HPLC) on retention time around 6. When the natural phosphate DNA was on the 3' end the degradation rate was at least 12 times faster than the degradation of the oligo with the phosphoramidate linkage introduced on the 3' end. Under the same experimental conditions, the oligonucleotide (ODN2) containing one phosphoramidimidate modification at each end had a degradation time 10 times longer than oligo with the natural phosphate DNA on the 3' end, indicating significantly increased resistance against the 3' exonuclease SVPDE by less formation of the mono-nucleotide and the appearance a new peak at 7.7 retention time corresponding to a dinucleotide. This suggests that SVPDE can jump one nucleotide unit from the 3' end and degrade the natural phosphate linkage.

Example 10

Biological and Biochemical Activity

Because phosphoramidimidate possess a positively charged phosphate at biological pH (7-7.5), it is possible that the biological activity and cell uptake would be affected by this charge. Previous work showed that the bioactivity with cation-conjugated oligonucleotides have superior cellular uptake properties and facilitate endosomal release via the proton sponge mechanism, relative to negatively charged oligomers.

To explore the biological activity of phosphoramidimidate DNA, the non-toxic oligonucleotide delivery method known as "passive transfection" was used. This procedure does not require liposomes, electroporation, or microinjection for entry of the oligonucleotide into cells. The oligonucleotide and appropriate cells are placed in a growth media and tested for uptake.

A 5'-fluorescein chromophore tag was linked through a thiophosphate linkage to the phosphoramidimidate oligonucleotide. Using a thiophosphate linkage increases resistance toward degradation by nucleases and the fluorescein chromophore can be used to monitor cellular uptake using flow cytometry or microscopy. One of these modifications was introduced at the 3' end, and the remaining modifications were distributed in the middle of the oligonucleotide. HPLC studies showed that phosphoramidimidate modified oliogonucleotides have resistance against snake venom phosphodiesterase. This would not only increase resistance toward degradation by nucleases, but also enhance the uptake by generating positive charges on the 3' end of the oligo and help in binding to the cell membrane.

FACS Analysis

Uptake of the oligonucleotides by HeLa cells was measured by taking advantage of the fluorescein tag. The cells were seeded at approx. 1×105 cells/well (12 well plates) and incubated in DMEM media for 24 hours. The concentration of 5'-fluorescein labeled phosphoramidimidate DNA in HyPure Molecular Biology Grade Water was measured by UV spectroscopy. For transfection, the medium was replaced with Opti-MEM premixed with the ODNs at various concentrations (0.5, 1.0, and 3.0 μM) and the cells were incubated for 24 hours.

Flow cytometric data on at least 10,000 cells per sample was acquired on a Moflow flow-cytometer (Beckman Coulter) equipped with a single 488 nm argon laser and a 530/40 nm emission filter (Fluorescein). Raw flow cytometry data was visualized using Summit 4.3 software (BeckmanCoulter). Fluorescence intensity of the 5'-fluorescein tag was analyzed for cells presenting higher fluorescence than the background. The background was defined as the auto fluorescence of cells. FACS analysis was obtained in HeLa cells for the 5'-fluorescein labeled ODN:

6-FAM-P(S)-T*GT AAA CCA TG*A T*GT GCT GCT* wherein * is a phosphoramidimidate modification; and 6-FAM-P(S)- is a 6-Carboxyfluorescein thioimidate FACS analysis was also obtained for HeLa cells transfected for 24 h with this ODN at 0.5 μM, 1.0 μM, and 3.0 μM.

Figure 7:
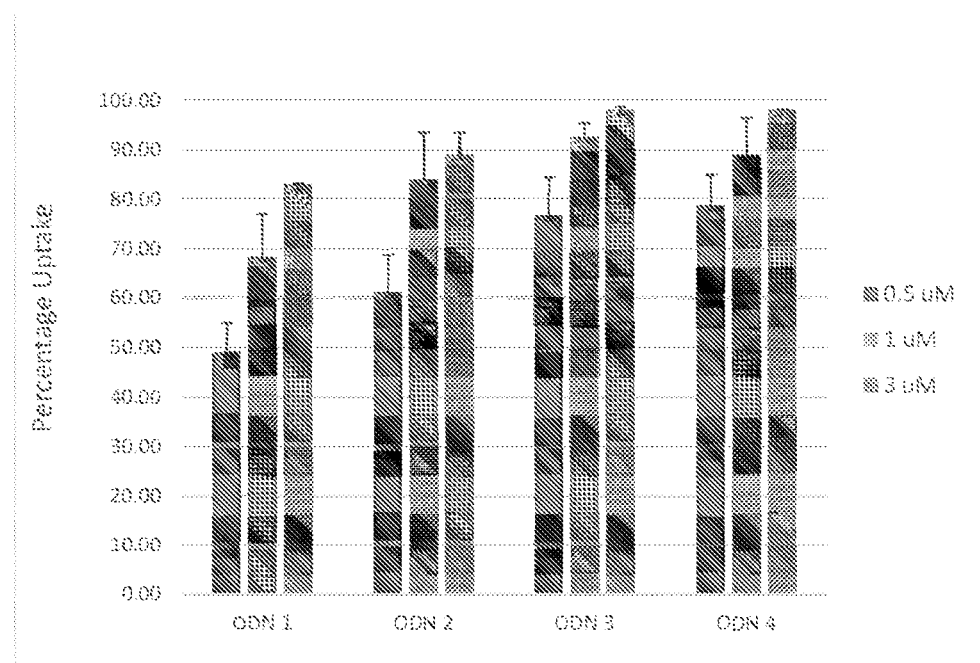
FIG. 7 shows the summary of results of fluorescently-labeled single-stranded DNA uptake into Hela cells after 24-hour transfection in the absence of a lipid transfecting agent.

As shown in FIG. 7, fluorescently-labeled single-stranded DNA were efficiently taken up into Hela cells for 24 hour transfection in the absence of a lipid transfecting agent. In FIG. 7:

ODN 1 is 6-FAM-P(S)- T*GT AAA* CCA TGA T*GT GCT GCT*A;

ODN 2 is 6-FAM-P(S)- T*GT* AAA CCA TG*A T*GT GCT GCT* A;

ODN 3 is 6-FAM-P(S)- T*GT* A*AA CC*A TGA T*GT GCT GCT *A;

ODN 4 is 6-FAM-P(S)- T*GT* AA*A C*CA TG*A T*GT GCT GCT* A;

wherein * is a phosphoramidimidate modification; and 6-FAM-P(S) is a 6-Carboxyfluorescein thioimidate.

As shown in FIG. 7, 50% of cells showed cell uptake when ODN1 with 4 modifications was used at 0.5 μM concentration. When the concentration was increased to 1.0 μM and 3.0 μM for the same ODN, the uptake increased to 68% and 80% respectively. With oligonucleotides having 5, 6, or 7 phosphoramidimidate modifications the uptake increased, but saturation was obtained at 3 μM with ODN3 and ODN4. This observation suggests oligomers having 6 and 7 phosphoramidimidate modifications are maximally transfected at 3 μM. Additionally, even at 0.5 μM these ODNs are taken up by 80% of the HeLa cells. Also of interest was the observation that ODN1 with only four modifications transfects 50% of the HeLa cells even at 0.5 μM, which suggests that increasing the number of modifications does not improve uptake because almost 98% of the cells take up the oligos at 3 μM concentration for both 6 and 7 modifications.

Microscope Imaging

The transfection experiments showing a significant uptake of phosphoramidimidate DNA could be explained by the presence of cationic phosphate which interacts with phospholipids on cell surfaces and thus facilitates transfection. However, an alternative explanation is that these oligomers were only on the surface of the cell membrane. FACS analysis are simply ionically interacting with phospholipids on cell surfaces and do not undergo transfection. This question was addressed using a confocal microscope to examine the location of the fluorescein tag on the oligonucleotides. HeLa cells were first seeded in DMEM medium containing 10% FBS at $0.1 \times 10^6$ cells/well in 4-well chambered cover slides (Thermo Scientific). After 24 hours at 60% confluency, the medium was removed and the cells were washed twice (0.5 mL D-PBS/wash) before transfection. A stock solution of ODNs was diluted to the desired concentration in OptiMEM and this transfection solution (250 µL) was added to each well. Cells were then incubated at 37° C. for 24 hours and then washed twice with (0.5 mL D-PBS). Cells were stained with Hoechst 33258 to visualize nuclei and with 1×CellMask™ Orange Plasma Membrane Stain to stain and show the cell membrane boundaries. Cells were analyzed in OptiMEM using a confocal microscope. The microscopy results showed that fluorescently labeled single-stranded IAOs were efficiently taken up into Hela cells after 24 hours transfection in the absence of lipid transfecting agent.

Example 11

Hydrolysis of RNA Heteroduplexes with *E. coli* RNase H1

The search for antisense and diagnostic DNA analogs has led to a wide range of DNA modifications but few of these modified DNAs possess the necessary properties for therapeutic antisense activity:activation of RNase H, an ability to form sequence-specific duplexes with complimentary oligoribonucleotides, and resistance towards nucleases. The inventors investigated whether phosphoramidimidate DNA could activate RNase H1 and therefore perform various oligonucleotide therapeutic activities.

Phosphoramidimidate derivatives of this disclosure were tested for their ability to stimulate RNase H1 activity. Thus, a 5'-fluorescein labeled RNA and complementary phosphoramidimidate ODNs were combined and treated with RNase H1. The positive control was natural DNA complementary to the same RNA, which should form a duplex that activates RNA degradation. The negative control was 2'-O-methyl RNA in duplex with the same RNA, which should not stimulate RNase H1 activity. Two samples of each duplex were incubated in 35 µL of the assay buffer (50 mM tris-HCl (pH 8.0), 20 mM KCl, 9 mM $MgCl_2$, 1 mM mercaptoethanol, and 250 µg/mL bovine serum albumin). *E. coli* RNase H1 (3 units) was added to one of each duplex sample and the assay kept at 25° C. for 12 hours. The other sample for each assay was not treated with RNase H1. The reaction mixtures were then diluted with an equal volume of 80% formamide gel loading buffer containing tracking dyes and analyzed by polyacrylamide gel electrophoresis (PAGE) (20%, 19:1 crosslinking, 7 M urea). The developed gels were analyzed using a Phosphorimager.

The oligonucleotides synthesized and tested were:

```
ODN1:  TGA^Me GT^MeC A^MeCA^Me T^MeGA^Me TT^MeC T^MeGA ^MeT

ODN2:  TGA^Me GT^MeC A^MeCA TGA^Me TT^MeC T^MeGA ^MeT

ODN3:  TGA GTC ACA TGA TTC TGA T
```

```
ODN4:  TGA^Me GT^MeC A^MeCA* T*GA^Me TT^MeC T^MeGA ^MeT

ODN5:  TGA* GT*C A*CA* T*GA* TT*C T*GA *T

ODN6:  TGA* GT*C A*CA TGA* TT*C T*GA *T
```

Figure 8:
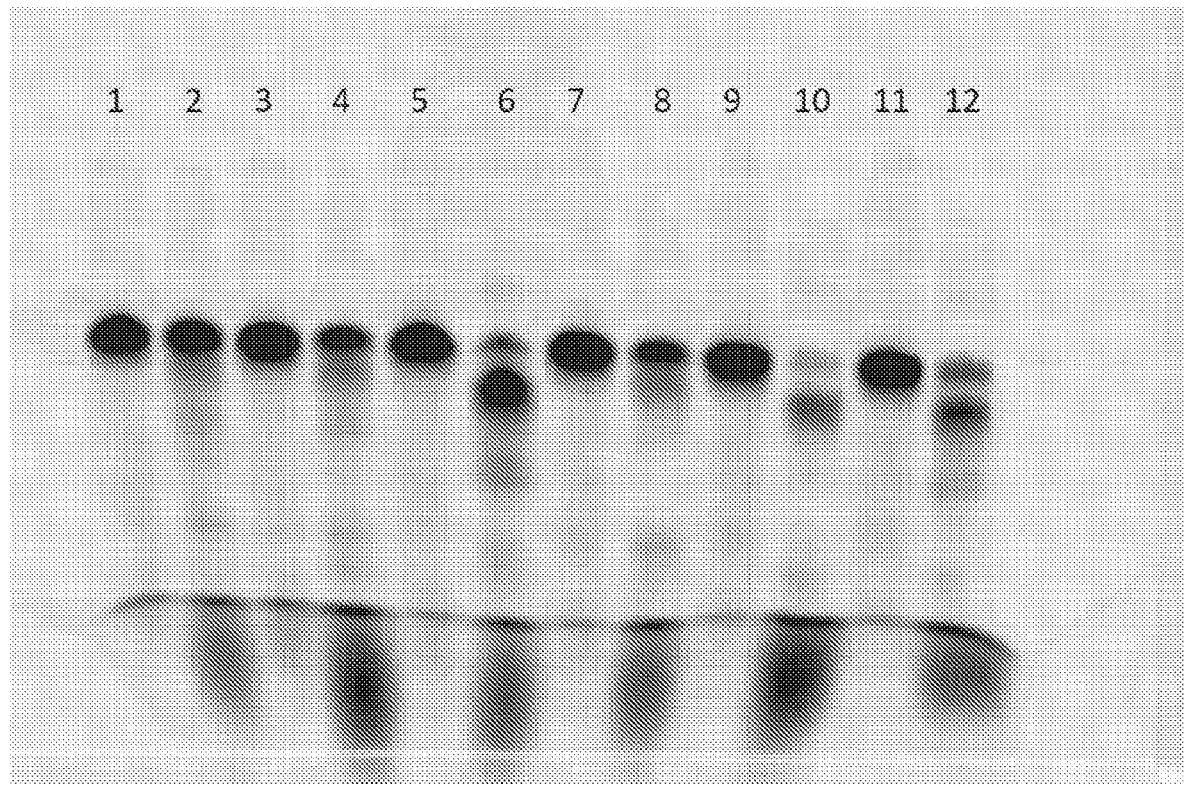
FIG. 8 shows denaturing polyacrylamide gel electrophoresis for *E. coli* RNase H1 degradation of RNA. 5'-Fluorescein labeled RNA was allowed to form duplexes with complementary ODNs (1-6), which were then treated with E. coli RNase H1 for 8 h and analyzed by PAGE.

In FIG. 8:

Lane 1 is 2'-O-methyl RNA ODN1/RNA.

Lane 2 is 2'-O-methyl RNA ODN1/RNA, enzyme.

Lane 3 is 2'-O-methyl RNA ODN2/RNA.

Lane 4 is 2'-O-methyl RNA ODN2/RNA, enzyme.

Lane 5 is ODN3/RNA.

Lane 6 is ODN3/RNA, enzyme.

Lane 7 is 2'-Omethyl and IAO4/RNA.

Lane 8 is 2'-Omethyl and IAO4/RNA, enzyme.

Lane 9 is ODN5/RNA.

Lane 10 is ODN5/RNA, enzyme.

Lane 11 is ODN6/RNA.

Lane 12 is ODN6/RNA enzyme.

As shown in FIG. 8, under these conditions, the ODN duplex remains intact in the absence of the enzyme RNase H1 (lanes 1,3,5,7,9,11). DNA modified with an alternating 2'-O-methyl linkage also remains intact (lane 2) but oligonucleotides modified with four natural phosphate linkages in the middle of the oligonucleotide stimulated RNA degradation (lane 4). The oligonucleotide in Lane 6 had natural phosphate linkages and therefore activated degradation. The oligonucleotides with phosphoramidimidate linkages (Lanes 8, 10, 12) stimulated RNA degradation indicating that phosphoramidimidate linkages are RNase H1 active.

The foregoing examples of the present invention have been presented for purposes of illustration and description. Furthermore, these examples are not intended to limit the invention to the form disclosed herein. Consequently, variations and modifications commensurate with the teachings of the description of the invention, and the skill or knowledge of the relevant art, are within the scope of the present invention. The specific embodiments described in the examples provided herein are intended to further explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

What is claimed is:

1. An oligomer comprising a monomer subunit comprising the chemical structure of formula I:

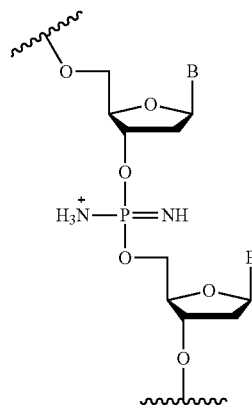

(formula I)

wherein:
each B is independently a nucleic acid base or a nucleic acid base protected with a silyl protecting group or an acid-labile or base-labile protecting group.

2. The oligomer of claim 1, wherein the nucleic acid base protecting group is selected from:

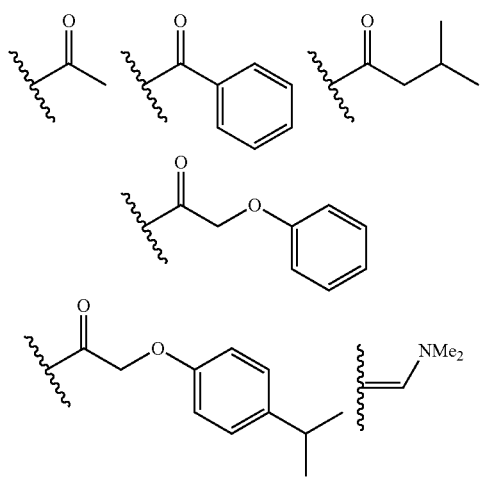

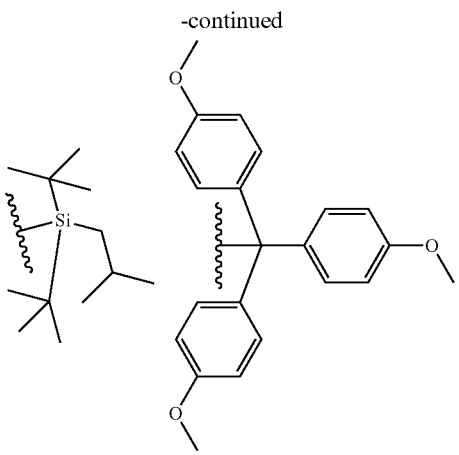

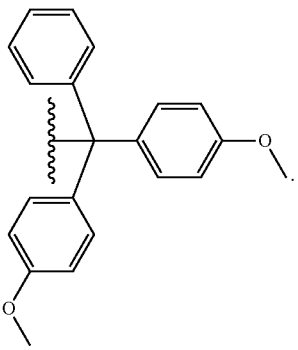

3. The oligomer of claim 1, comprising between 2 and 40 monomeric subunits.

4. An oligonucleotide of claim 1 comprising phosphoramidimidate internucleotide linkages that readily form duplexes with complementary DNA or RNA.

5. An oligonucleotide of claim 1, wherein the nucleic acid base is selected from: adenosine, guanosine, uracil, thymine, cytosine, or inosine.

* * * * *